(12) United States Patent
Clements et al.

(10) Patent No.: US 8,815,865 B2
(45) Date of Patent: *Aug. 26, 2014

(54) SUBSTITUTED 4-HYDROXYPYRIMIDINE-5-CARBOXAMIDES

(75) Inventors: Matthew J. Clements, Old Bridge, NJ (US); John S. Debenham, Scotch Plains, NJ (US); Jeffrey J. Hale, Westfield, NJ (US); Christina Madsen-Duggan, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 22 days.

This patent is subject to a terminal disclaimer.

(21) Appl. No.: 13/379,536

(22) PCT Filed: Jun. 21, 2010

(86) PCT No.: PCT/US2010/039289
§ 371 (c)(1),
(2), (4) Date: Dec. 20, 2011

(87) PCT Pub. No.: WO2011/002623
PCT Pub. Date: Jan. 6, 2011

(65) Prior Publication Data
US 2012/0108600 A1    May 3, 2012

Related U.S. Application Data

(60) Provisional application No. 61/221,789, filed on Jun. 30, 2009, provisional application No. 61/237,491, filed on Aug. 27, 2009.

(51) Int. Cl.
*A61K 31/501* (2006.01)
*A61K 31/4965* (2006.01)
*C07D 401/06* (2006.01)
*C07D 239/02* (2006.01)

(52) U.S. Cl.
USPC ............ 514/252.02; 514/255.05; 544/238; 544/319

(58) Field of Classification Search
None
See application file for complete search history.

(56) References Cited

U.S. PATENT DOCUMENTS

| 7,323,475 B2 | 1/2008 | Arend et al. |
| 2008/0124740 A1 | 5/2008 | Evdokimov et al. |
| 2008/0171756 A1 | 7/2008 | Shaw et al. |

FOREIGN PATENT DOCUMENTS

| WO | WO2007038571 | 4/2007 |
| WO | WO2008094292 | 8/2008 |
| WO | WO2009117269 | 9/2009 |
| WO | WO 2009117269 A1 * | 9/2009 |

* cited by examiner

*Primary Examiner* — Svetlana M Ivanova
(74) *Attorney, Agent, or Firm* — Matthew A. Leff; Valerie J. Camara

(57) ABSTRACT

The present invention relates to substituted 4-hydroxypyrimidine-5-carboxamides useful as HIF prolyl hydroxylase inhibitors to treat anemia and like conditions.

4 Claims, No Drawings

SUBSTITUTED 4-HYDROXYPYRIMIDINE-5-CARBOXAMIDES

CROSS REFERENCE TO RELATED APPLICATIONS

This application is a U.S. National Phase application under 35 U.S.C. §371 of PCT Application No. PCT/US2010/039289, filed Jun. 21, 2010, which claims priority under 35 U.S.C. §119(e) from U.S. Provisional Application Ser. No. 61/221,789, filed Jun. 30, 2009 and U.S. Provisional Application Ser. No. 61/237,491, filed Aug. 27, 2009.

BACKGROUND OF THE INVENTION

The insufficient delivery of oxygen to cells and tissues is associated with anemia, which is defined as a deficiency in the blood's oxygen-carrying capacity, and ischemia, in which restrictions in blood supply are caused by a constriction or blockage of blood vessels. Anemia can be caused by the loss of red blood cells (hemorrhage), excessive red blood cell destruction (hemolysis) or deficiencies in erythropoiesis (production of red blood cells from precursors found in the bone marrow). The symptoms of anemia can include weakness, dizziness, fatigue, pallor, impairment of cognitive function and a general reduction in quality of life. Chronic and/or severe anemia can lead to the exacerbation of myocardial, cerebral or peripheral ischemia and to heart failure. Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

The primary pharmacological treatment for anemia is administration of some variant of recombinant human erythropoietin (EPO). For anemias associated with kidney disease, chemotherapy-induced anemia, anemia from HIV-therapy or anemia due to blood loss, recombinant EPO is administered to enhance the supply of the hormone, correct the shortage of red blood cells and increase the blood's oxygen-carrying capacity. EPO replacement is not always sufficient to stimulate optimal erythropoiesis (e.g., in patients with iron processing deficiencies) and has associated risks.

Hypoxia-inducible factor (HIF) has been identified as a primary regulator of the cellular response to low oxygen. HIF is a heterodimeric gene transcription factor consisting of a highly regulated α-subunit (HIF-α) and a constitutively expressed β-subunit (HIF-β, also known as ARNT, or aryl hydrocarbon receptor nuclear transporter). HIF target genes are reported to be associated with various aspects of erythropoiesis (e.g., erythropoietin (EPO) and EPO receptor), glycolysis and angiogenesis (e.g., vascular endothelial growth factor (VEGF)). Genes for proteins involved in iron absorption, transport and utilization as well as heme synthesis are also targets of HIF.

Under normal oxygenation, HIF-α is a substrate in a reaction with molecular oxygen, which is catalyzed by a family of iron(II)-, 2-ketoglutarate- and ascorbate-dependent dioxygenase enzymes called PHD-1 (EGLN2, or egg laying abnormal 9 homolog 2, PHD2 (EGLN1), and PHD3 (EGLN3). Proline residues of HIF-α are hydroxylated (e.g., Pro-402 and Pro-564 of HIF-1α) and the resulting product is a target of the tumor suppressor protein von-Hippel Lindau, a component of an E3 ubiquitin ligase multiprotein complex involved in protein ubiquitination. Under low oxygenation, the HIF-α hydroxylation reaction is less efficient and HIF-α is available to dimerize with HIF-β. HIF dimers are translocated to the cell nucleus where they bind to a hypoxia-responsive enhancer element of HIF target genes.

Cellular levels of HIF are known to increase under conditions of hypoxia and after exposure to hypoxia mimetic agents. The latter includes, but is not limited to, specific metal ions (e.g., cobalt, nickel, manganese), iron chelators (e.g., desferrioxamine) and analogs of 2-ketoglurate (e.g., N-oxalyl glycine). The compounds of the present invention inhibit the HIF prolyl hydroxylases (PIED-1, PHD-2, PHD-3) and can also serve to modulate HIF levels. These compounds therefore have utility for the treatment and/or prevention of disorders or conditions where HIF modulation is desirable, such as anemia and ischemia. As an alternative to recombinant erythropoietin therapy, the compounds of the present invention provide a simpler and broader method for the management of anemia.

SUMMARY OF THE INVENTION

The present invention concerns compounds of formula I

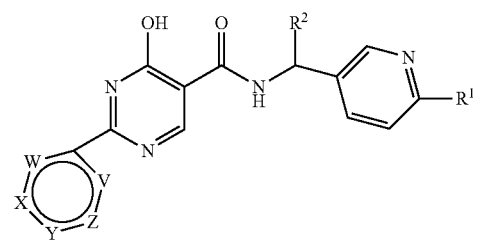

which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

DETAILED DESCRIPTION OF THE INVENTION

The present invention provides compounds of formula I or a pharmaceutically acceptable salt thereof, or a stereoisomer thereof, or a pharmaceutically acceptable salt of the stereoisomer thereof:

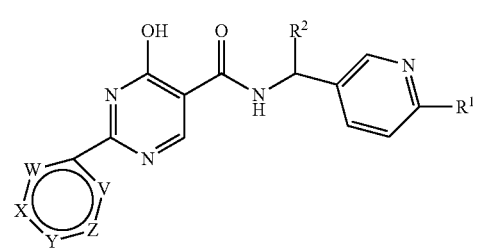

$R^1$ is selected from $-C_{1-10}$ alkyl, $-C_{2-10}$ alkenyl, $-C_{2-10}$ alkynyl, and $-C_{1-6}$ alkoxy, wherein in $R^1$ said alkyl, alkenyl, alkynyl, and alkoxy are each optionally substituted with 1, 2, or 3 $R^8$ substituents;

$R^2$ is selected from $C_{3-8}$ cycloalkyl and $C_{3-8}$ heterocycloalkyl, optionally substituted with 1, 2, or 3 substituents selected from halo, hydroxyl, and $-OC_{1-10}$ alkyl;

V, W, X, Y, and Z are each independently selected from N and CH, wherein V, W, X, Y or Z is substituted with one or two nitrogens, and at least one of V or W must be N; and $R^8$ is selected from halogen, hydroxyl, —$C_{1-10}$ alkyl, —$C_{1-10}$ alkenyl, —$C_{1-10}$ alkynyl, cyano, oxo, difluoromethoxy, trifluoromethoxy, and 2,2,2-trifluoroethoxy.

An illustrative but nonlimiting example of compounds of the invention are (R) 4-Hydroxy-N-[(6-methoxypyridin-3-yl)(tetrahydro-2H-pyran-4-yl)methyl]-2-pyridazin-3-ylpyrimidine-5-carboxamide; (S) 4-Hydroxy-N-[(6-methoxypyridin-3-yl)(tetrahydro-2H-pyran-4-yl)methyl]-2-pyridazin-3-ylpyrimidine-5-carboxamide; 4-Hydroxy-N-[(6-methoxypyridin-3-yl)(tetrahydro-2H-pyran-4-yl)methyl]-2-pyridazin-3-ylpyrimidine-5-carboxamide; or a pharmaceutically acceptable salt or mixtures thereof.

In one embodiment of the invention, $R^1$ is selected from —$C_{1-10}$ alkyl, —$C_{2-10}$ alkenyl, and $C_{2-10}$ alkynyl, wherein in $R^1$ said alkyl, alkenyl, and alkynyl, are each optionally substituted with 1, 2, or 3 $R^8$ substituents.

In another embodiment of the invention, $R^1$ is selected from —$C_{1-10}$ alkyl and —$C_{1-6}$ alkoxy, said alkyl, and alkoxy are each optionally substituted with 1, 2, or 3, $R^8$ substituents.

In another embodiment of the invention, $R^1$ is selected from —$C_{1-6}$ alkoxy optionally substituted with 1, 2, or 3 $R^8$ substituents. In a variant of this embodiment $R^1$ is methoxy.

In one embodiment of the invention, $R^2$ is $C_{3-8}$ cycloalkyl, optionally substituted with 1, 2, or 3 substituents selected from halo, hydroxyl, and —$OC_{1-10}$ alkyl. In a variant of this embodiment, $C_{3-8}$cycloalkyl is chosen from cyclopropyl, cyclobutyl, cyclopentyl, cyclohexyl, and cycloheptyl, optionally substituted with 1, 2, or 3 substituents selected from halo, hydroxyl, and —$OC_{1-10}$ alkyl.

In one embodiment of the invention, $R^2$ is $C_{3-8}$ heterocloalkyl, optionally substituted with 1, 2, or 3 substituents selected from halo, hydroxyl, and —$OC_{1-10}$ alkyl. In a variant of this embodiment, $R^2$ is chosen from morpholino, morpholinyl, piperidino, piperidyl, pyrrolidinyl, pyrrolidino, uretidinyl, oxanyl, oxolanyl, dioxanyl, thiomorpholino, pyrazolidinyl, piperidinyl, and piperazinyl and $R^2$ is optionally substituted with 1, 2, or 3 substituents selected from halo, hydroxyl, and —$OC_{1-10}$ alkyl. In yet another variant of this embodiment, $R^2$ is oxanyl.

In one embodiment of the invention, W is N and V, X, Y, and Z are each CH. In one embodiment, W and X are N. In another embodiment of the invention, W and Y are N. In yet another embodiment of the invention, W and Z are N.

In one embodiment of the invention, V is N and W, X, Y, and Z are each CH. In another embodiment of the invention, V and Z are N. In another embodiments of the invention, V and Y are N. In yet another embodiment of the invention, W and X are N.

In another embodiment of the invention, W and V are N and X, Y, and Z are each CH.

The compounds of this invention, particularly Example 1, where $R^1$ is methoxy, $R^2$ is oxanyl, W=X=N and V, Y and Z are each CH or V=Z=N and W, X and Y are each CH provides for an unexpectedly more desirable pharmacokinetic profile relative to the structurally relevant examples (Example 163 and Example 190) disclosed in International PCT application PCT/US09/036,501, filed Mar. 9, 2009.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "alkoxy" represents a linear or branched alkyl group of indicated number of carbon atoms attached through an oxygen bridge.

The term "$C_{3-5}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "heterocycle" (and variations thereof such as "heterocycle" or "heterocyclyl") broadly refers to (i) a stable 4- to 8-membered, saturated or unsaturated monocycle ring, and the ring system contains one or more heteroatoms (e.g., from 1 to 6 heteroatoms, or from 1 to 4 heteroatoms) selected from N, O and S and a balance of carbon atoms (the monocycle ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Non limiting examples of heterocyclylic moieties include, but are not limited to, the following: carbazolyl, carbolinyl, furanyl, imidazolyl, indolazinyl, isobenzofuryl, isoquinolyl, isothiazolyl, isoxazolyl, naphthpyridinyl, oxadiazolyl, oxazolyl, oxazoline, isoxazoline, oxetanyl, pyranyl (oxanyl), pyrazinyl, pyrazolyl, pyridazinyl, pyridopyridinyl, pyridinyl, pyrimidyl, pyrrolyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrofuryl, dihydroimidazolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, and tetrahydrothienyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

"Heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. The group may be a terminal group or a bridging group.

Unless otherwise specifically noted as only "unsubstituted" or only "substituted", or when substituents are specifically enumerated, cycloalkyl, aryl (including phenyl) and heterocycle (including heteroaryl) groups are unsubstituted or substituted. As used herein, the terms "substituted $C_3$-$C_{10}$ cycloalkyl", "substituted aryl (including phenyl)" and "substituted heterocycle" are intended to include the cyclic group containing from 1 to 3 substituents in addition to the point of attachment to the rest of the compound.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

When any variable (e.g., $R^2$, $R^3$, etc.) occurs more than one time in any substituent or in formulas I-III, its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

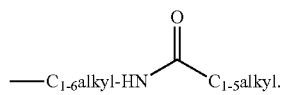

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

Structural representations of compounds having substituents terminating with a methyl group may display the terminal methyl group either using the characters "CH$_3$", e.g. "—CH$_3$" or using a straight line representing the presence of the methyl group, e.g., "—", i.e.,

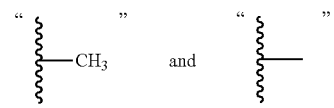

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

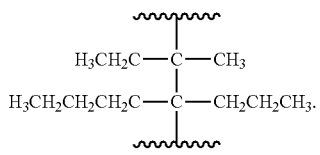

Optical Isomers-Diastereomers-Geometric Isomers-Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts and solvates thereof. Unless specifically mentioned otherwise, reference to one isomer applies to any of the possible isomers. Whenever the isomeric composition is unspecified, all possible isomers are included. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxyl —$CH=C(OH)$— groups (enol forms). Both keto and enol forms, individually as well as mixtures thereof, are included within the scope of the present invention.

Salts

Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydro-scopicity and solubility. The term "pharmaceutically acceptable salts" refers to salts prepared from pharmaceutically acceptable non-toxic bases or acids. When the compound of the present invention is acidic, its corresponding salt can be conveniently prepared from inorganic bases or organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from organic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from inorganic or organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono-, sesqui-, di- and trihydrates.

Prodrugs

The present invention includes within its scope the use of prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

Utilities

Compounds of the present invention are inhibitors of hypoxia-inducible factor (HIF) prolyl hydroxylases, and as such are useful in the treatment and prevention of diseases and conditions in which HIF modulation is desirable, such as anemia and ischemia. Compounds of the invention can be used in a selective and controlled manner to induce hypoxia-inducible factor stabilization and to rapidly and reversibly stimulate erythropoietin production and secretion. Accordingly, another aspect of the present invention provides a method of treating or preventing a disease or condition in a mammal, the treatment or prevention of which is effected or facilitated by HIF prolyl hydroxylase inhibition, which comprises administering an amount of a compound of Formula I that is effective for inhibiting HIF prolyl hydroxylase. This aspect of the present invention further includes the use of a compound of Formula I in the manufacture of a medicament for the treatment or prevention of a disease or condition modulated by HIF prolyl hydroxylase.

In one embodiment is a method of enhancing endogenous production of erythropoietin in a mammal which comprises administering to said mammal an amount of a compound of Formula I that is effective for enhancing endogenous production of erythropoietin.

Another embodiment is a method of treating anemia in a mammal which comprises administering to said mammal a therapeutically effective amount of a compound of Formula I. "Anemia" includes, but is not limited to, chronic kidney disease anemia, chemotherapy-induced anemia (e.g., anemia resulting from antiviral drug regimens for infectious diseases, such as REV and hepatitis C virus), anemia of chronic disease, anemia associated with cancer conditions, anemia resulting from radiation treatment for cancer, anemias of chronic immune disorders such as rheumatoid arthritis, inflammatory bowel disease, and lupus, and anemias due to menstruation or of senescence or in other individuals with iron processing deficiencies such as those who are iron-replete but unable to utilize iron properly.

Another embodiment is a method of treating ischemic diseases in a mammal, which comprises administering to said mammal a therapeutically effective amount of a compound of Formula I.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., anemia.

Pharmaceutical Composition

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or a pharmaceutically acceptable salt or solvate thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other active ingredients known to be useful for improving the level of erythropoietin in a patient.

Abbreviations Used in the Description of the Preparation of the Compounds of the Present Invention

| | |
|---|---|
| AcOH | Acetic acid |
| aq | Aqueous |
| brine | Saturated aqueous sodium chloride solution |
| CDI | 1,1'-carbonyldiimidazole |
| CO | Carbon monoxide |
| DCM | Dichloromethane |
| Dppf | 1,1''-bis(diphenylphosphino)ferrocene |
| DBU | 1,8-diazabicyclo[5.4.0]undec-7-ene |
| DIEA | N,N-diisopropylethylamine |
| DMAP | 4-N,N-dimethylaminopyridine |
| DMF | NN-dimethylformamide |
| DMSO | Dimethyl sulfoxide |
| EtOAc | Ethyl acetate |
| Et (et) | Ethyl |
| EtOH | Ethanol |
| Et$_2$O or ether | Diethyl ether |
| g | Grams |
| h or hr | Hour |
| HATU | O-(7-Azabenzotriazol-1-yl)-N,N,N',N'-tetramethyluronium hexafluorophosphate |
| HCl | Hydrochloric acid |
| HPLC | High-performance liquid chromatography |
| i-PrOH or IPA | Isopropyl alcohol |

-continued

| | |
|---|---|
| m-CPBA | 3-chloroperbenzoic acid |
| mg | Milligrams |
| mL | Milliliters |
| mmol | Millimole |
| MeCN | Acetonitrile |
| MeOH | Methanol |
| min | Minutes |
| ms or MS | Mass spectrum |
| MTBE | Methyl tert-butyl ether |
| μg | Microgram(s) |
| μL | Microliters |
| NaHSO$_4$ | sodium bisulfate |
| NaOEt | Sodium ethoxide |
| NaOMe | Sodium methoxide |
| Na$_2$SO$_4$ | Sodium sulfate |
| NH$_4$Cl | Ammonium chloride |
| NH$_4$OH | Ammonium hydroxide |
| PPTS | Pyridinium p-toluenesulfonate |
| R$_f$ | Retention time |
| rt | Room temperature |
| TEA | Triethylamine |
| TFA | Trifluoroacetic acid |
| THF | Tetrahydrofuran |

General Methods

Reactions sensitive to moisture or air were performed under nitrogen using anhydrous solvents and reagents. The progress of reactions was determined by either analytical thin layer chromatography (TLC) performed with E. Merck pre-coated TLC plates, silica gel 60F-254, layer thickness 0.25 mm or liquid chromatography-mass spectrum (LC-MS). Analytical HPLC/MS—Standard Method: Mass analysis was performed on a Waters Micromass® ZQ™ with electrospray ionization in positive ion detection mode. High performance liquid chromatography (HPLC) was conducted on an Agilent 1100 series HPLC on Waters C18 XTerra 3.5 μm 3.0×50 mm column with gradient 10:90-100 v/v CH$_3$CN/H$_2$O+v 0.05% TFA over 3.75 min then hold at 100 CH$_3$CN+v 0.05% TFA for 1.75 min; flow rate 1.0 mL/min, UV wavelength 254 nm (all HPLC/MS data was generated with this method unless indicated otherwise). Analytical HPLC/MS—Basic Method: Mass analysis was performed on a Waters Micromass® ZQ™ with electrospray ionization in positive ion detection mode. High performance liquid chromatography (HPLC) was conducted on an Agilent 1100 series HPLC on Waters C18 XBridge 3.5 μm 3.0×50 mm column with gradient 10:90-98:2 v/v CH$_3$CN/H$_2$O+v 0.025% NH$_4$OH over 3.25 min then hold at 98:2 CH$_3$CN+v 0.025% NH$_4$OH for 2.25 min; flow rate 1.0 mL/min, UV wavelength 254 nm. Concentration of solutions was carried out on a rotary evaporator under reduced pressure. Flash chromatography was performed using a Biotage Horizon or SP1 Flash Chromatography apparatus (Dyax Corp.) on silica gel (32-63 μM particle size, KP-Sil 60 Å packing material type) in pre-packed cartridges or using an ISCO CombiFlash™ Sq 16× or CombiFlash®Companion™ apparatus on silica gel (32-63 μM, 60 Å) in pre-packed cartridges. Microwave reactions were carried out on a Biotage Initiator™ 2.0 or CEM Discover™ system.

Intermediate 1

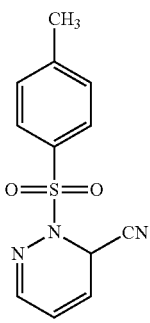 [SMILES: Cc1ccc(S(=O)(=O)N2N=CC=CC2C#N)cc1]

2-[(4-methylphenyl)sulfonyl]-2,3-dihydropyridazine-3-carbonitrile

A solution of pyridazine (1.807 mL, 24.98 mmol), aluminum chloride (0.010 g, 0.075 mmol) and trimethylsilyl cyanide (6.03 mL, 45.0 mmol) in DCM (30 mL) was stirred under a nitrogen atmosphere at 0° C. for 20 min. A solution of p-toluenesulfonyl chloride (8.19 g, 43.0 mmol) in DCM (60 mL) was added dropwise over 1 h. The reaction was warmed to room temperature, stirred for an additional 65 h and concentrated. The residue was treated with EtOH (50 mL) and the resulting solids were filtered to afford the title compound. HPLC/MS: 262.1 (M+1); $R_t$=2.51 min.

Intermediate 2

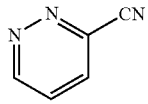

Pyridazine-3-carbonitrile

To the product of Intermediate 1 (4.98 g, 19.06 mmol) in THF (50 mL) was added DBU (3.59 mL, 23.82 mmol). The reaction was stirred at room temperature under a nitrogen atmosphere for 1 h. Saturated aq. $NH_4Cl$ (50 mL) was added and the reaction was poured into water (50 mL). The aqueous medium was extracted with EtOAc, dried ($MgSO_4$), filtered and concentrated. The residue was purified by flash chromatography on silica gel gradient eluted with 0-50% EtOAc/hexane to afford the title compound. HPLC/MS: 106.2 (M+1); $R_t$=0.38 min.

Intermediate 3

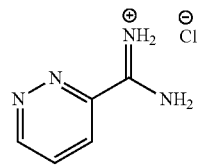

Amino(pyridazin-3-yl)methaniminium chloride

To the product of Intermediate 2 (1.7 g, 16.18 mmol) in MeOH (10 mL) was added sodium methoxide (0.370 mL, 1.618 mmol, 25 wt % in MeOH). The reaction was stirred at room temperature overnight when ammonium chloride (0.952 g, 17.79 mmol) was added. The reaction was refluxed for 2.5 h, cooled to room temperature, diluted with MeOH and concentrated to afford the title compound. HPLC/MS: 123.1 (M+1); $R_t$=0.34 min.

Intermediate 4

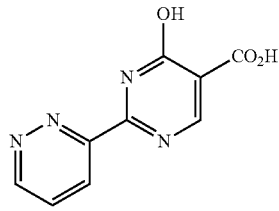 [SMILES: O=C(O)c1cnc(-c2cccnn2)nc1O]

4-Hydroxy-2-pyridazin-3-ylpyrimidine-5-carboxylic acid

To the product of Intermediate 3 (0.500 g, 3.15 mmol) in EtOH (8.0 mL) was added diethyl ethoxymethylenemalonate (0.637 mL, 3.15 mmol) and sodium methoxide (0.793 mL, 3.47 mmol, 25 wt % in MeOH). The reaction was heated in a microwave for 10 min at 120° C. Additional diethyl ethoxymethylenemalonate (0.319 mL, 1.576 mmol) was added and the reaction was heated in a microwave for 10 min at 120° C. Potassium hydroxide (4.73 mL, 9.46 mmol, 2.0 M) was added and the reaction was heated in a microwave for 10 min at 120° C. The reaction was diluted with water and concentrated. The residue was dissolved in a minimal volume of water and extracted with EtOAc. The aqueous layer was adjusted to pH=2 using conc. aq. HCl and stirred for 15 min. The solids were filtered and rinsed with water and hexane to afford the title compound. HPLC/MS: 219.0 (M+1); $R_t$=0.28 min (Basic Method).

Example 1

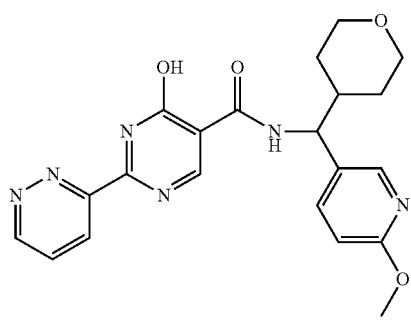

E-1

(R)- or (S)-4-Hydroxy-N-[(6-methoxypyridin-3-yl)(tetrahydro-2H-pyran-4-yl)methyl]-2-pyridazin-3-ylpyrimidine-5-carboxamide (E-1)

Scheme 1

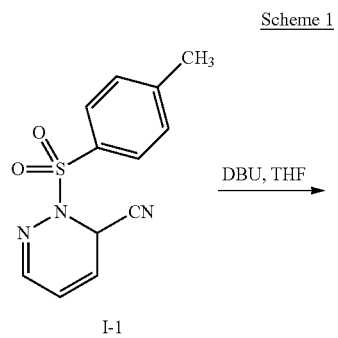

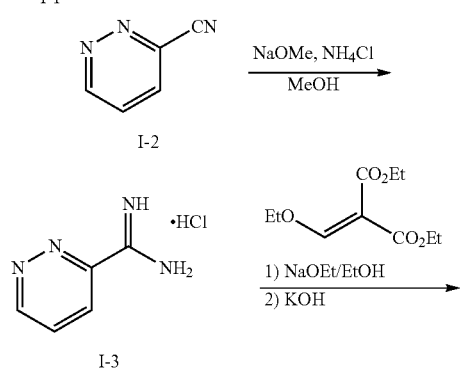

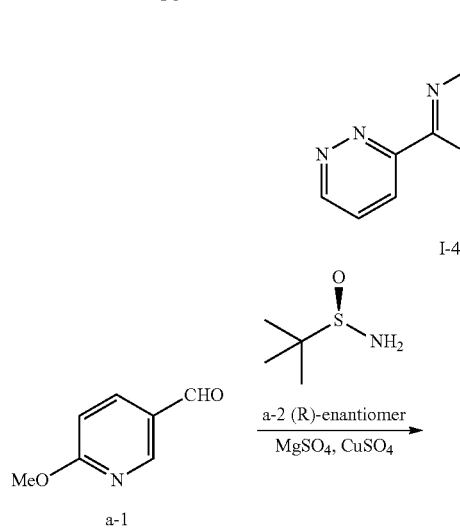

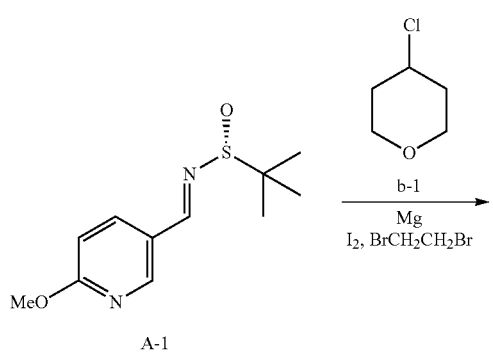

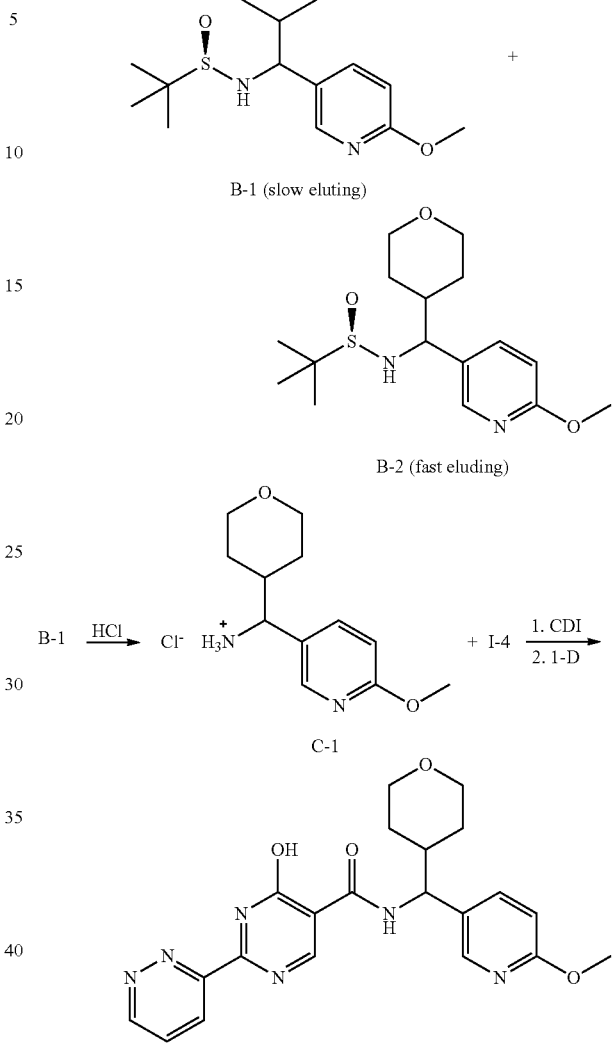

Step A: (R)—N-[(1E)-(6-methoxypyridin-3-yl)methylene]-2-methylpropane-2-sulfinamide (A-1)

6-Methoxynicotinaldehyde, (a-1), (20.0 g, 146 mmol) and (R)-(+)-2-methyl-2-propanesulfinamide, (a-2), (21.2 g, 175 mmol) were dissolved in chloroform (140 mL) and PPTS (1.8 g, 7.3 mmol), magnesium sulfate (17.6 g, 146 mmol) and copper(II)sulfate (46.6 g, 292 mmol) were added. The mixture was heated to 65° C. overnight. The material was allowed to cool and was filtered through a Solka Floc pad and concentrated under vacuum. The material was purified by flash chromatography on silica gel gradient eluted with 0-40% EtOAc in hexane affording the product (1-A). HPLC/MS: 241.0 (M+1); $R_f$=2.84 min.

Step B: (R)—N-[(6-methoxypyridin-3-yl)(tetrahydro-2H-pyran-4-yl)methyl]-2-methylpropane-2-sulfinamide (B-1)

Mg (10.6 g, 438 mmol) was dispersed in THF (160 mL) and 1 crystal of $I_2$ and 1,2-dibromoethane (0.25 mL) were added. 4-Chlorotetrahydro-2H-pyran, dissolved in THF (50 mL), was added dropwise and the mixture was heated at 70° C. for 1.5 h. The solution was cooled to 0° C. and the product from step A was added dropwise as a solution in toluene (100 mL). The reaction was aged at rt for 2 h and the mixture was filtered eluting with MTBE. The reaction was quenched with sat. $NH_4Cl$ (aq) and extracted twice with EtOAc. The organic layers were combined and washed with brine, dried with $Na_2SO_4$, filtered and concentrated. The resulting oil was purified by flash chromatography on silica gel gradient eluted with 100% EtOAc to 8% MeOH in EtOAc affording the desired slow eluting diastereomer, (B-1). HPLC/MS: 327.1 (M+1); $R_t$=2.31 min. The fast eluting isomer on silica gel (B-2) was also isolated. HPLC/MS: 327.1 (M+1); $R_t$=2.15 min Step C: (R) or (S) 1-(6-methoxypyridin-3-yl)-1-(tetrahydro-2H-pyran-4-yl)methanamine hydrochloride (C-1)

The slow eluting diastereomer from Step B, (B-1), (14.7 g, 44.9 mmol) was dissolved in DCM (100 mL) and MeOH (100 mL) and HCl in dioxane (2 M, 33.7 mL, 67.3 mmol) was added slowly to keep temperature below 35° C. The reaction was stirred at rt for 1 h and additional HCl (3 mL) was added. The reaction was stirred 30 min more and HCl (3 mL) was again added. The reaction was stirred a final 30 min more and the material was concentrated affording the product. HPLC/MS: 223.0 (M+1); $R_t$=0.65 min Step D: (R) or (S) 4-Hydroxy-N-[(6-methoxypyridin-3-yl)(tetrahydro-2H-pyran-4-yl)methyl]-2-pyridazin-3-ylpyrimidine-5-carboxamide (E-1)

Intermediate 4 (4-Hydroxy-2-pyridazin-3-ylpyrimidine-5-carboxylic acid) (8.8 g, 40.3 mmol) was dissolved in NMP (45 mL) and TEA (11.2 mL, 81 mmol) was added and the slurry was aged for 15 min at rt. CDI (7.2 g, 44.4 mmol) was added and the reaction was heated at 70° C. for 1 h. To the hot solution was added in one portion the solid amine product from step C, (C-1), and heating was continued for an additional 4 h and the reaction was allowed to come to rt overnight. The mixture was diluted with water and TEA (7.6 mL, 40.5 mmol) and the aqueous layer was extracted twice with EtOAc. The resulting aqueous portion was brought to about pH 5.5 using HCl (2 M, aq) and was extracted with two portions of $CHCl_3$.

The combined $CHCl_3$ portion was washed with brine, dried with $Na_2SO_4$, filtered and concentrated. The product was purified by preparative HPLC/MS as follows: Mass analysis was performed on a Waters Micromass® ZQ™ with electrospray ionization in positive ion detection mode. High performance liquid chromatography (HPLC) was conducted on a Waters preparative HPLC system on Waters C18 XBridge 5 µm 50×100 mm column with gradient 10:90-22:78 v/v $CH_3CN/H_2O$ (pH=10 with $NH_4OH$) over 11 min; flow rate 100 mL/min, UV wavelength 210-400 nm. The desired fractions were concentrated affording the title compound. HPLC/MS: 423.1 (M+1); $R_t$=2.01 min. $^1H$ NMR (500 MHz, DMSO-$d_6$): δ 10.87 (d, J=8.41 Hz, 1H); 9.35 (dd, J=4.96, 1.65 Hz, 1H); 8.58 (s, 1H); 8.39 (dd, J=8.55, 1.65 Hz, 1H); 8.10 (d, J=2.40 Hz, 1H); 7.86 (dd, J=8.56, 4.98 Hz, 1H); 7.64 (dd, J=8.57, 2.47 Hz, 1H); 6.80 (d, J=8.55 Hz, 1H); 4.84 (t, J=8.18 Hz, 1H); 3.87 (dd, J=11.41, 3.98 Hz, 1H); 3.89-3.71 (m, 4H); 3.38-3.28 (m, +$H_2O$); 2.03-1.95 (m, 1H); 1.64 (d, J=13.08 Hz, 1H); 1.32-1.22 (m, 4H).

Comparative Examples

The pharmacokinetics of Example 1 (E-1) was evaluated, and compared to that of Example 163 and Example 190 both disclosed in International PCT Application, No. PCT/US09/036,501, filed Mar. 9, 2009. Compounds were formulated in a 1:1 solution (by volume) of PEG200: water and dosed at 0.5 mg/kg of body weight. The formulation was dosed intravenously in 2 dogs (beagles), and blood was drawn at the following time points (hours) 0.08, 0.25, 0.5, 1, 2, 4, 6, 8, 24. The plasma concentrations shown in the table below were determined by protein precipitation followed by liquid chromatography—tandem mass spectrometry analysis.

| Time (hours) | Example 1 (E-1) mean concentration (µM) | Example 163 PCT/US09/036501 mean concentration (µM) | Example 190 PCT/US09/036501 mean concentration (µM) |
|---|---|---|---|
| 0.08 | 2.228 | 2.188 | 13.203 |
| 0.25 | 2.058 | 1.340 | 8.861 |
| 0.50 | 1.959 | 1.248 | 7.971 |
| 1.00 | 1.660 | 1.558 | 7.392 |
| 2.00 | 1.394 | 1.385 | 6.827 |
| 4.00 | 1.323 | 0.774 | 6.079 |
| 6.00 | 0.917 | 0.450 | 10.071 |
| 8.00 | 0.504 | 0.332 | 9.031 |
| 24.00 | 0.100 | 0.656 | 2.872 |
| Cl (mL/min/kg) | 1.35 | — | 0.100 |
| MRT (h) | 7.93 | — | 16.3 |
| T ½ (h) | 6.07 | — | 9.98 |

The example of the present invention in which $R^2$ is tetrahydro-2H-pyran-4-yl and $R^1$ is methoxy shows the unexpected benefit of having a 13.5-fold faster intrinsic clearance with concomitant decrease in mean residence time (MRT) and half-life (t½) relative to Example 190 of PCT/US09/036,501. A faster clearance improves the safety profile of a compound by reducing the time it takes for the drug to be removed from circulation would reduce the potential for a patient to experience an adverse event.

The other example of PCT/US09/036,501 (Example 163) showed the plasma concentration to be increasing 24 hours after dosing. This unfavorable type of pharmacokinetic profile may indicate the potential for dose accumulation and may complicate the safe dosing of the compound. Example 1 (E-1) of the current invention shows improvements on these pharmacokinetic aspects.

Biological Assays

The exemplified compound, Examples 1 of the present invention, has been found to inhibit the interaction between PHD2 and a HIF peptide and exhibit $IC_{50}$ values ranging between 0.1 nanomolar to 10 micromolar. Non-limiting examples of assays that may be useful to detect favorable activity are disclosed in the following publications: Oehme, F., et al., *Anal. Biochem.* 330:74-80 (2004); Hirsilä, M, et al., *J. Bio. Chem.* 278 (33): 30772-30780 (2005); Hyunju, C., et al., *Biochem. Biophys. Res. Comm.* 330 (2005) 275-280; and Hewitson, K. S., et al., *Methods in Enzymology*, (Oxygen Biology and Hypoxia); Elsevier Publisher (2007), pg. 25-42 (ISSN: 0076-6879).

The biological activity of the present compound may be evaluated using assays described herein below:

To each well of a 96-well plate was added 1 µL of test compound in DMSO and 20 µl of assay buffer (50 mM Tris pH 7.4/0.01% Tween-20/0.1 mg/ml bovine serum albumin/ 10 µM ferrous sulfate/1 mM sodium ascorbate/20 µg/ml catalase) containing 0.15 µg/ml FLAG-tagged full length PHD2 expressed in and purified from baculovirus-infected Sf9 cells. After a 30 min preincubation at room temperature, the enzymatic reactions were initiated by the addition of 4 µL of substrates (final concentrations of 0.2 µM 2-oxoglutarate and 0.5 µM HIF-1α peptide biotinyl-DLDLEMLAPYIPMD-DDFQL). After 2 hr at room temperature, the reactions were terminated and signals were developed by the addition of a 25 µL quench/detection mix to a final concentration of 1 mM ortho-phenanthroline, 0.1 mM EDTA, 0.5 nM anti-$(His)_6$ LANCE reagent (Perkin-Elmer Life Sciences), 100 nM AF647-labeled streptavidin (Invitrogen), and 2 µg/ml $(His)_6$-VHL complex (S. Tan (2001) Protein Expr. Purif. 21, 224-234). The ratio of time resolved fluorescence signals at 665 and 620 nm was determined, and percent inhibition was calculated relative to an uninhibited control sample run in parallel.

Inhibition of the catalytic activity of HIF-PHD1 and HIF-PHD3 can be determined similarly.

The PHD2 binding activity expressed as $IC_{50}$ (nM), for the compounds of the present invention disclosed in Example 1 was found to be ≤10 nM.

What is claimed is:

1. A compound selected from the group consisting of: (R)-4-Hydroxy-N-[(6-methoxypyridin-3-yl)(tetrahydro-2H-pyran-4-yl)methyl]-2-pyridazin-3-ylpyrimidine-5-carboxamide; (S) 4-Hydroxy-N-[(6-methoxypyridin-3-yl)(tetrahydro-2H-pyran-4-yl)methyl]-2-pyridazin-3-ylpyrimidine-5-carboxamide; 4-Hydroxy-N-[(6-methoxypyridin-3-yl)(tetrahydro-2H-pyran-4-yl)methyl]-2-pyridazin-3-ylpyrimidine-5-carboxamide; and a pharmaceutically acceptable salt thereof.

2. A compound according to claim 1 selected from the group consisting of: (R)-4-Hydroxy-N-[(6-methoxypyridin-3-yl)(tetrahydro-2H-pyran-4-yl)methyl]-2-pyridazin-3-ylpyrimidine-5-carboxamide and a pharmaceutically acceptable salt thereof.

3. A compound according to claim 1 selected from the group consisting of: (S)-4-Hydroxy-N-[(6-methoxypyridin-3-yl)(tetrahydro-2H-pyran-4-yl)methyl]-2-pyridazin-3-ylpyrimidine-5-carboxamide and a pharmaceutically acceptable salt thereof.

4. A compound selected from the group consisting of: 4-Hydroxy-N-[(6-methoxypyridin-3-yl)(tetrahydro-2H-pyran-4-yl)methyl]-2-pyridazin-3-ylpyrimidine-5-carboxamide; and a pharmaceutically acceptable salt thereof.

* * * * *